United States Patent [19]
Warburton et al.

[11] Patent Number: 5,250,171
[45] Date of Patent: Oct. 5, 1993

[54] SENSOR FOR CARBON MONOXIDE

[75] Inventors: Piers R. G. Warburton; Daryle H. Busch, both of Lawrence, Kans.

[73] Assignee: University of Kansas, Lawrence, Kans.

[21] Appl. No.: 698,169

[22] Filed: May 10, 1991

[51] Int. Cl.$^5$ .................................. G01N 27/26
[52] U.S. Cl. ............................ 204/431; 204/432; 204/412; 204/153.16
[58] Field of Search ........... 204/412, 431, 432, 153.16, 204/153.1, 400, 424

[56] References Cited

U.S. PATENT DOCUMENTS 4,797,180  1/1989  Schneider et al. .................. 204/412

FOREIGN PATENT DOCUMENTS 2094005  8/1982  United Kingdom .

OTHER PUBLICATIONS

Potentiometric Behavior of the Cooper Electrode in Aqueous Copper(II) Perchlorate Solutions Containing Sodium Chloride; Analytical Chimica Acta 234 (1990) 331–338.
Journal of Organomettalic Chemistry; 44 (1972); Carbonyl Chemistry of the Group IB Metals: M. I. Bruce, pp. 209–226.
Absorption of Carbon Monoxide by Cuprous Ammonium Salts; Industrial and Engineering Chemistry, vol. 22, No. 4 (1930), pp. 382–384.
CA 51–Fossil Fuels, vol. 106, 1987, Carbon Suboxide.
Instrumental Methods in Electrochemistry, Potential Step Techniques; Sec. 2.4, pp. 49–50, 26–32, 398–400, 396–397.
Complex Formation of Copper (I) Perchlorate with Ethylene or Carbon Monoxide in Water and Isolation of Related Complexes; Inorganic Chemistry, vol. 15, No. 9, 1976, pp. 2301–2303.

*Primary Examiner*—John Niebling
*Assistant Examiner*—Bruce F. Beil
*Attorney, Agent, or Firm*—Hovey, Williams, Timmons & Collins

[57] ABSTRACT

An electrochemical carbon monoxide detecting method and apparatus (10, 46) is disclosed which can detect carbon monoxide levels as low as about 500 ppm and which has excellent selectivity and a linear response over a broad range of carbon monoxide concentrations. The apparatus (10, 46) employs an electrical cell assembly (12, 54) having an electrolyte (20, 60) containing hydrated Cu(II) ions therein; upon creation of a constant magnitude potential difference between the cell electrodes (22, 24) ranging from about +0.03 – +0.15 V, the Cu(II) ions are reduced to Cu(I) ions, and the latter react with carbon monoxide to form Cu(I)-carbonyl complexes. Detection of an electrical parameter indicative of the Cu(II)-Cu(I) reduction permits quantitative carbon monoxide determinations. Preferably, the detecting apparatus (14) is amperometric, employing a potentiostat (28) and output device (38). Alternately, detection can be accomplished potentiometrically.

24 Claims, 2 Drawing Sheets

SENSOR FOR CARBON MONOXIDE

BACKGROUND OF THE INVENTION

1. Field of the Invention

The present invention is broadly concerned with an apparatus and method for the sensing and detection of carbon monoxide in gaseous mixtures. More particularly, it is concerned with such an apparatus and method of high sensitivity, selectivity and response range, whereby the invention provides a means of detecting and quantifying if desired carbon monoxide present in a wide variety of test samples. The invention makes use of the specificity of coordination electrochemistry, and in practice employs an electrical cell having electrolyte with hydrated Cu(II) ions therein; an electrical potential difference of appropriate magnitude is created between the cell electrodes, so that the Cu(II) ions are reduced to Cu(I) ions which react with carbon monoxide in the test sample to form Cu(I)-carbonyl complexes. An electrical parameter indicative of the reduction of Cu(II) ions to Cu(I) ions (e.g., the response current generated between the electrodes where the potential difference therebetween is maintained at a constant magnitude) is detected as a means of determining the presence and concentration of carbon monoxide in the test sample.

2. Description of the Prior Art

In recent years there has been a rapid growth in the development and use of chemical sensors for a wide range of chemical species. One particular area for which a number of devices have been commercially available for several years is for the detection of oxidizable gases such as carbon monoxide.

Carbon monoxide detection is of importance from two principle standpoints. The first is toxicity, which derives from the ability of carbon monoxide to preferentially bind to hemoglobin in place of oxygen, resulting in a legal work-place exposure limit of 50 ppm. The second is the analysis of the exhaust and flue emissions from the combustion of fossil fuels, both from considerations of optimization of engine/boiler performance as well as pollution control.

Apart from purely chemical methods, such as following the progression of a color change along a sample tube, carbon monoxide is usually selectively monitored (as opposed to total combustibles) using either infrared absorption or amperometrically in an electrochemical cell. The latter typically use a high surface area electrode behind a gas permeable membrane, held at a potential greater than that required for carbon monoxide oxidation. This ensures that the current measured is mass transport limited and, therefore, proportional to the carbon monoxide concentration. Since the oxidation of carbon monoxide requires very positive potentials, these sensors frequently also respond to other oxidizable gases such as hydrogen or methane.

The chemical literature contains a wealth of coordination chemistry involving small molecules and, in principle, such reactions could impart high selectivity for a particular species by a chemical sensor. There are a number of commercially available electrochemical sensors which use coordination chemistry to achieve selectivity for the desired analyte. Examples include ion selective electrodes (Koryta, *Anal. Chem. Acta*, 233, 1, (1990); Koryta et al., *Ion Selective Electrodes*, 2nd Edition; Freiser, *Ion-Selective Electrodes In Analytical Chemistry*, Vols. 1 & 2) and a recent amperometric sensor for carbon dioxide (Evans et al., *Journal of Electroanalytical Chemistry*, 262, 119, (1989); *Analytical Chemistry*, 61, 577 (1989)).

The literature also contains many examples of the interaction of carbon monoxide and Cu(I); also, coordination of olefins with Cu(I) has been reported. For example, the absorption of carbon monoxide by aqueous solutions containing Cu(I) halide solutions has been known for over a century, and in the intervening years an extensive technology for carbon monoxide separation and purification has been developed based on these systems. Almost all of these techniques involve use of Cu(I) in the presence of a variety of ligands such as chloride, ammonia, lactate, etc. Some work has been done in near neutral solution in the absence of other complexing ligands; these studies include the preparation and isolation of $Cu_2(CO)_2SO_4$ by Joannis (*Comptes Rendes Hebdomadaires des Seances del Academie des Sciences*, 125, 9948 (1897)), by reacting copper sulfate solution and finely divided copper in the presence of carbon monoxide, and, more recently, isolation of Cu(I) carbonyl as the perchlorate salt (Ogura, *Inorganic Chemistry*, 15, 2301 (1976)). Other examples of the synthesis of Cu(I) carbonyl complexes can be found in the review by Bruce (*Journal of Organometallic Chemistry*, 44, 209 (1972)). The Cu(I) carbonyl species present in aqueous solution is dependent upon experimental conditions. For example, Busch et al. (*Inorganic Chemistry*, 18, 521, (1979)) concluded from potentiometric experiments that the principle Cu(I) carbonyl species present in hydrochloric acid solution is $CuCOCl_2$. Souma et al. (*Inorganic Chemistry*, 15, 969 (1970)) report that in aqueous $BF_3$, $Cu(CO)_n^+$ is formed, where n=1 to 4, and their studies have also shown that Cu(CO)X can be prepared in acidic solution, where X is $Cl-$, $HSO_4^-$, etc. It would appear that a variety of Cu(I) carbonyl species can be generated, and the equilibria between them is dependent upon experimental conditions. This parallels the versatile chemistry of Cu(I) complexes with halides, phosphines, etc., in nonaqueous solvents.

U.K. published application No. 2,094,005 describes an electrochemical gas sensor for the detection of carbon monoxide. In this system, at the anode, carbon monoxide is electrochemically oxidized, whereas at the cathode a reduction occurs, so that the overall cell reaction is $CO + \frac{1}{2}O_2 = CO_2$. The sensor apparatus makes use of stacked electrodes and an electrolyte supply, with appropriate wick(s) being employed to ensure operative contact between the electrolyte and electrodes.

SUMMARY OF THE INVENTION

The present invention provides an apparatus and method for the qualitative or quantitative determination of the presence of carbon monoxide in a test sample. Broadly speaking, use is made of an electrical cell assembly including a quantity of electrolyte having hydrated Cu(II) ions therein, and a pair of electrodes in operative contact with the electrolyte. The carbon monoxide detecting means is electrically coupled with the electrodes for creating a potential difference therebetween of a magnitude preferentially favoring the reduction of Cu(II) ions to Cu(I) ions and the formation of Cu(I)-carbonyl complexes by reaction between the Cu(I) ions and carbon monoxide present in the test sample. Structure is also provided for detecting an electrical parameter indicative of the reduction of Cu(II) ions to Cu(I) ions.

In preferred forms, the sensor operates amperometrically, wherein a constant magnitude potential difference is maintained between the cell electrodes and the response current generated between the electrodes is measured and analyzed to give carbon monoxide content of a test sample. In alternative forms, the sensor may operate potentiometrically, by the simple expedient of placing a high impedance voltmeter between the cell electrodes and directly measuring potential difference.

DESCRIPTION OF THE PREFERRED EMBODIMENTS

Figure 1:
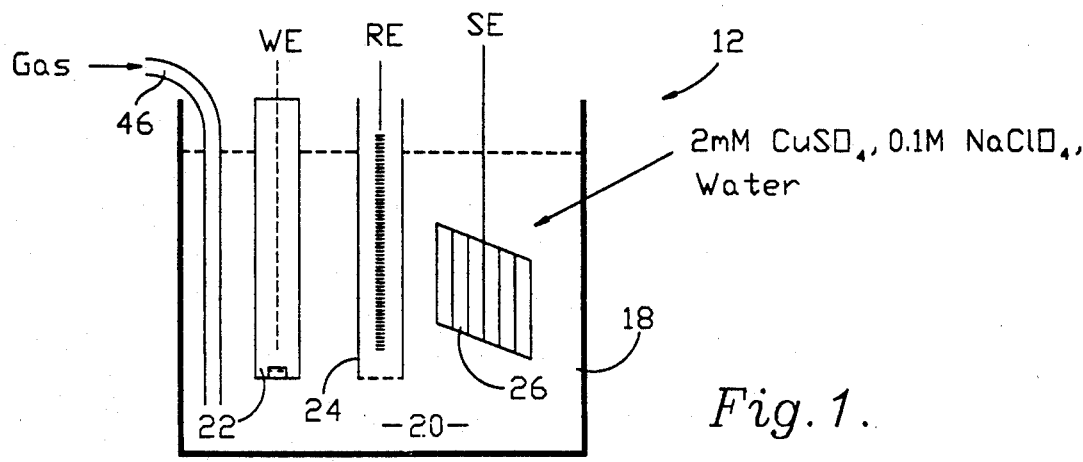
FIG. 1 is a schematic representation of a laboratory-type electrochemical cell assembly useful in accordance with the invention for the detection of carbon monoxide.
Figure 2:
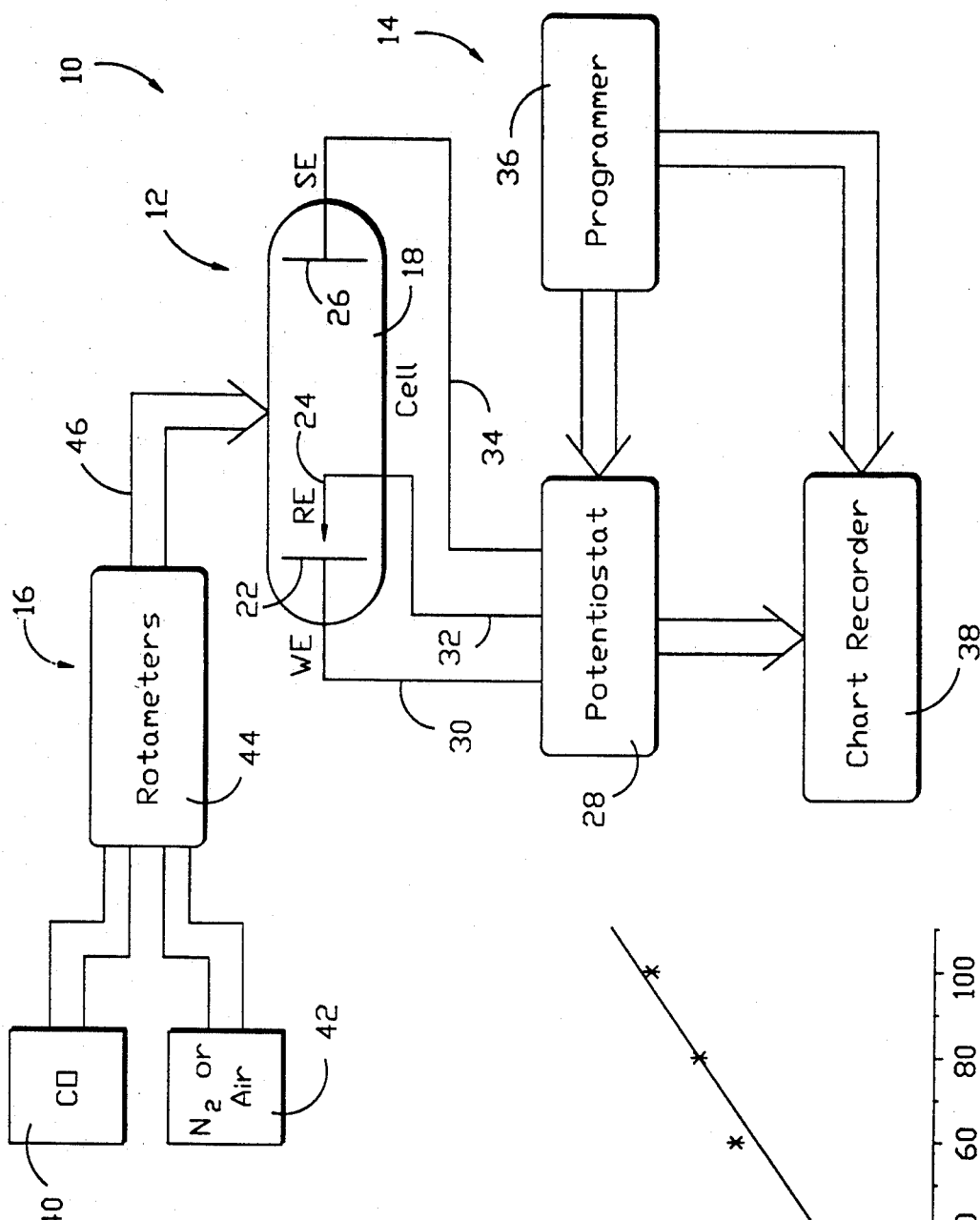
FIG. 2 is a schematic diagram illustrating the interconnection of the cell illustrated in FIG. 1 with carbon monoxide detecting apparatus and means for introducing test samples into the cell.

Turning now to the drawings, and particularly FIGS. 1 and 2, a carbon monoxide detection apparatus 10 is illustrated which broadly includes an electrochemical cell assembly 12, as well as detecting means 14 electrically coupled with the cell 12, and structure broadly referred to by the numeral 16 for introducing a test sample into cell 12.

In more detail, the cell 12 in the form shown in FIGS. 1-2, includes an upright vessel or beaker 18 holding a supply of electrolyte 20. In addition, a total of three electrodes are immersed within the electrolyte 20, namely a working electrode 22, reference electrode 24 and secondary electrode 26.

The electrolyte 20 is preferably a solution of copper sulfate (0.5 mM to 10 mM, most preferably 2 mM) in water, along with a quantity of sodium perchlorate (0.01M to 1M, most preferably 0.1M). Alternately, other salts of Cu(II) ions could be employed, so long as they are non-coordinating in aqueous systems, i.e., the anion of the salt must not materially affect the potential of the Cu couples more than plus or minus 30 millivolts. Exemplary Cu salts useful in this context include the $PF_6$, perchlorate, tetrafluoroborate, nitrate and trifluoromethylsulfate salts. In like manner, a variety of supporting electrolytes can also be used, for example those taken from the group consisting of sodium perchlorate, sodium trifluoroacetate, sodium tetrafluoroborate, sodium trifluoromethylsulfate, potassium hexafluorophosphate, sodium sulfate, sodium acetate, potassium hydrogen phosphate, potassium phthalate, methylsulfonate, phenylsulfonate, nitrate salts, and mixtures thereof.

For best operation of the sensor apparatus, the supporting electrolyte should be present in a substantial excess relative to the copper salt, for example from about 10 to 100 times the concentration of the copper salt. Similarly, the concentration of Cu(II) ions in the overall electrolyte should be sufficiently in excess of the concentration of carbon monoxide in the test sample to assure that mass transfer of carbon monoxide determines the rate of formation of the Cu(I)-carbonyl complexes.

The electrolyte 20 should also exhibit a pH of up to about 6.5, more preferably from about 1 to 6, and most preferably from about 4 to 6. In order to obtain such acid pH levels, the electrolyte would typically be supplemented with a mineral acid (e.g., $H_2SO_4$) or the corresponding acid to the supplemental electrolyte. If the pH of the electrolyte becomes basic, the copper salt may precipitate, whereas if the system is too acidic, the magnitude of the desired signal becomes too small.

The electrolyte 20 may also include organic solvents such as methanol, ethanol or acetone, but the entire system should be essentially free of interfering amounts of anionic or neutral species which will coordinate with Cu(I) ions.

The working electrode 22 is preferably formed of glassy carbon, although a platinum disk sealed into KelF (Bioanalytical Systems) or glass may be used for the working electrode. The reference electrode 24 is advantageously a saturated calomel electrode (SCE), such as a Radiometer K401 SCE. Finally, the secondary electrode 26 has a large surface area and is formed of platinum wire/gauze. Before each experiment, the disc electrodes were polished with a 0.05 micron alumina slurry, rinsed and briefly held in an ultrasonic bath in the solvent of the experiment, to ensure complete alumina removal. For electrolysis experiments, a two compartment cell was used, with the compartments being separated by a glass frit. Otherwise, a single compartment cell was generally used.

The detecting means 14 in the illustrated embodiment includes a conventional potentiostat 28 (Princeton Applied Research Model 173) fitted with a Princeton Digital Coulometer Module Model 179. As illustrated, the potentiostat 28 is connected via appropriate leads 30, 32 and 34 to the working electrode 22, reference electrode 24 and secondary electrode 26 respectively. A Princeton Applied Research universal programmer (Model 175) 36 is operatively connected with the potentiostat 28, and is used in cyclic coltammetry studies; the programmer 30 is not required for normal carbon monoxide detecting operations. Finally, an output device such as chart recorder 38 is operatively coupled to potentiostat 28 and programmer 36 in order to provide a readout indicative of carbon monoxide concentration in a given test sample.

The sample introduction structure 16, in the test apparatus of FIGS. 1-2, includes a supply of carbon monoxide 40 as well as a supply 42 of nitrogen or air. These supply vessels are coupled to conventional rotameters 44 serving to create a dedired gas mixture, with the rotameters being connected through a gas delivery conduit 46 leading to and discharging into the electrolyte 20.

During cyclic voltammetry testing with the apparatus of FIGS. 1-2, it was determined that a potential difference between the working and reference electrodes of from about +0.03 to +0.15 volts, and more preferably about +0.05 volts, preferentially favored the reduction of Cu(II) ions to Cu(I) ions, with the formation of Cu(I)-carbonyl complexes. Potential differences of differing magnitudes could favor competing reactions, such as the plating-out of copper. Accordingly, the above potential difference range is preferred for carbon monoxide detection.

It was also found that when the potential difference was maintained at a constant value of about +0.05 volts vs the SCE, and applying a steady stream of carbon monoxide to the cell, the current rose to a near constant value (the noise observed being due to the gas flow turbulence in the electrolyte solution), and upon replacing the carbon monoxide with nitrogen, the current returned to zero. Similar results were obtained using compressed air instead of nitrogen as the purging gas, thereby establishing the insensitivity of the system to oxygen. The times required to reach a constant current value after switching the delivered gas to either carbon monoxide or nitrogen were, typically, about 1 to 2 minutes and 5 to 10 minutes respectively, depending upon gas flow rate, cell volume and other operational parameters. Such results indicated no significant interaction between the bulk electrolyte and carbon monoxide beyond simple gas dissolution. Cyclic voltammograms using a platinum working electrode gave similar results to those obtained with a glassy carbon electrode, but the controlled potential experiments showed a gradual decrease in response with time, which was attributed to a slow poisoning of the platinum electrode by carbon monoxide.

Figure 3:
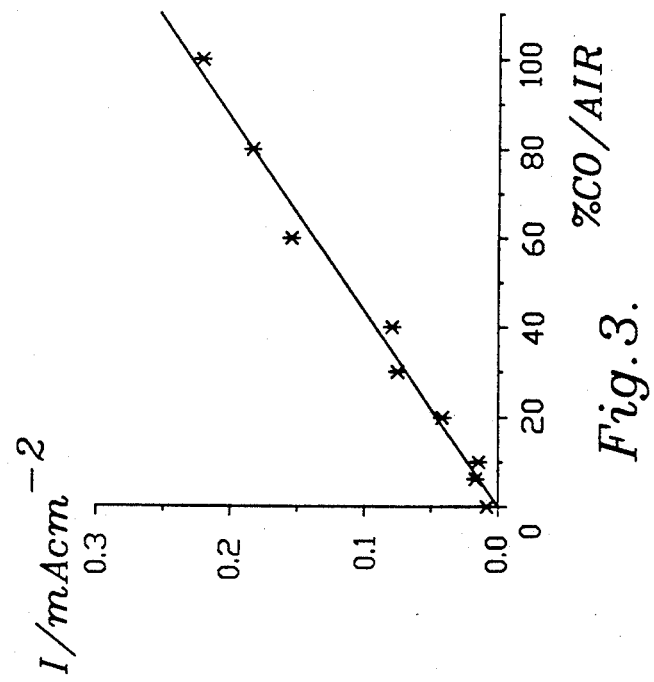
FIG. 3 is a graph depicting the steady state response current versus carbon monoxide concentration in air, generated using the apparatus depicted in FIGS. 1 and 2.

In another set of tests, various concentrations of carbon monoxide in air, over the range of 0-100% carbon monoxide, were tested using the FIGS. 1-2 apparatus, using the glassy carbon electrode at a potential of +0.05 volts vs the SCE and maintaining a constant gas flow rate with a fixed rate of stirring (magnetic stirrer). It was found that the response current varied linearly with carbon monoxide concentration for a cupric ion concentration between 1 mM and 10 mM. However, the response reached a plateau when the cupric ion concentration reached a concentration of 0.1 mM. The results of this series of tests are graphically depicted in FIG. 3, wherein the specific data points are noted by asterisks.

These results are consistent with the conclusion that the rate of reaction of the system is controlled by mass transport of the carbon monoxide. This is limited by the low solubility of carbon monoxide in water. Similarly, varying the Cu(II) ion concentration of a saturated carbon monoxide solution gave a linear response at low Cu(II) concentrations, which reached a plateau at higher concentrations in excess of about 1.5 mM.

At low carbon monoxide concentrations in the test samples (less than about 3% by volume) the background current became significant. A point by point current-/potential curve for a fixed gas flow rate of air, nitrogen and 1% carbon monoxide in air exhibited no significant difference between nitrogen and air, indicating that the background current was due primarily to the reduction of Cu(II) ion to copper metal, rather than oxygen reduction. By varying the potential and copper ion concentration, it was possible to increase the signal to background ratio, bearing in mind that a weak signal will be more sensitive to the effects of noise. With a copper sulfate concentration of 0.2 mM and a potential of +0.13 V vs SCE, it was possible to detect down to 500 ppm carbon monoxide in air, the sensitivity being defined as the total current that is twice the background.

The effect of temperature on response time with the FIGS. 1-2 apparatus in constant potential mode as described above was linear with increasing temperatures from 300° to 350° K. The rate of response time increase with temperature was large, as expected for a diffusion controlled process. The increase in response time over this temperature range indicates that the increase in rate of diffusion more than compensates for the lower solubility of carbon monoxide at higher temperatures.

Constant potential electrolysis experiments were performed with aqueous 2 mM Cu(II) ion in 0.1M sodium perchlorate with the solution saturated with carbon monoxide, giving a colorless solution. A graph of current versus accumulated charge, extrapolated to zero, confirmed a one electron reduction (+0.05 V vs SCE). As expected, there was no indication of reduction of carbon monoxide, a process known to occur at much more negative potentials. Cyclic voltammograms of the resulting solution exhibited a quasi-reversible oxidative process ($E_{\frac{1}{2}}$=mean of the anodic and cathodic peak potentials=0.15 V, delta Ep=140 mV, 10 mV/s), a result that is consistent with the formation of a Cu(I)-carbonyl complex.

The facilitated reduction of Cu(II) ion in the presence of carbon monoxide can also be followed potentiometrically, in principle offering an alternative mode of operation for a sensor. Graphs of potential at either a glassy carbon or graphite electrode showed approximately linear behavior for the natural logarithm of the carbon monoxide concentration with a slope of 28 mV, indicating a copper to carbonyl ratio of 1:1 (m=1), based on the Nernst equation. At very low carbon monoxide concentrations, the function deviated from linearity, presumably because of the onset of other redox processes.

Additional experiments were performed in order to confirm the identity of the copper carbonyl. A solution of carbonyl Cu(I) cation $CuCO^+$ was prepared by stirring aqueous copper sulfate in 0.1M aqueous sodium perchlorate (supporting electrolyte for electrochemical experiments) over copper powder under a carbon monoxide atmosphere. Cyclic voltammograms of the colorless solution ($E_{\frac{1}{2}}$=0.165 V, delta $E_p$=140 mV/s, 10 mV/s) were similar to those obtained after bulk electrolysis at +0.05 V vs SCE as described earlier. These experiments clearly indicate that the primary reaction of this sensing system is the electrochemical reduction of aqueous Cu(II) ion in the presence of carbon monoxide to form the well known $CuCO^+$.

The cyclic voltammetry of the $Cu^{2+}/CuCO^+$ reduction was not electrochemically reversible, whether starting from $Cu^{2+}$ or the copper carbonyl. Except at very low pH (less than 1.5), the reduction sweep $Cu^{2+}$ +CO (arrow heading to right) $CuCO^+$ appeared to be free of kinetic control. Potential step chronoamperometric experiments gave linear current versus inverse square root time plots which passed through the origin, indicating a diffusion controlled process. As discussed earlier, the response time of the carbon monoxide sensing system was fast, consistent with mass transport being the determining factor.

In contrast to the reduction sweep, the oxidation of $CuCO^+$ to $Cu^{2+}$ appeared to be more drawn out, with reduced peak height. At slow sweep rates and high pH, the Cu(II)/(I) couple became more reversible, as judged from the anodic and cathodic peak separations and relative heights. Plots of $[I_p{}^c/I_p{}^a]$ increased with sweep rate and were greater than unity over the range examined (10-200 mV/s), both characteristics of the electron transfer step being preceded by a rate determining chemical step process, a so called CE process.

At low pH, and/or fast sweep rates, the electrochemical irreversibility became markedly more pronounced.

The peak potentials of the cyclic voltammograms for aqueous Cu(II) ion in the presence of carbon monoxide exhibited a pH dependence. The mechanism of the electrochemical process is unclear, but observations are consistent with the reoxidation of cuprous carbonyl proceeding via initial loss of carbonyl ligand by associative attack by hydroxide ion, followed by electron transfer. This effect was manifested in the response behavior to carbon monoxide at constant potential (about +0.05 V vs SCE), with the signal decreasing at lower pH. For pH greater than about 6, the onset of copper hydroxide formation and precipitation drastically reduced the response current; an optimum for pH was about 5.

From the cyclic voltammetry, it would appear that the electron transfer step may also be kinetically limited. A plot of peak separation versus pH for the Cu(II)/(I) couple in the presence of carbon monoxide shows that the process becomes more reversible as the pH increases, but fails to become completely free of kinetic complications as indicated by the leveling off of the peak separation at about 100 mV for pH greater than about 4. This is probably due to the very different coordination geometries of Cu(I) and Cu(II).

Investigations were also carried out to determine the effect of selected supporting electrolytes from the class described previously. For each electrolyte, the potential of the Cu(II)/(I) carbon monoxide dependent peak in the cyclic voltammogram (100 mV/s) was determined over the pH range about 1 to 6. All of the electrolytes tested except halides showed pH dependences for the peak potentials of the Cu(II)/(I) reduction similar to that found with sodium perchlorate as the supporting electrolyte. The behavior of the electrolytes can be correlated with the ligating abilities of the anions. Those anions which are usually non-coordinating ($BF_4^-$, $ClO_4^-$, $CF_3SO_2^-$, $CF_3CO_2^-$, etc.) were found to give the most positive Cu(II)/(I) peak potentials, whereas weak ligands for Cu(II), for example acetate, phthalate and phosphate, gave more negative potentials. These last three are of importance, if the sensing system needed to be pH buffered. A more negative peak potential would decrease the signal to background ratio, lowering the sensitivity.

Ligands which bind Cu(I) preferentially were found to be unsuitable for use in this present invention. For example, when 0.1M potassium chloride is the electrolyte, the system shows no response to carbon monoxide. Because of the extensive literature involving complexes of the general form $Cu(CO)_nCl$, the effect of chloride concentration was determined in more detail by cyclic voltammetry, in the hope of finding some "symbiotically" favorable conditions. At low chloride concentrations (less than 1 mM), Cu(II) reduction peaks were observed giving rise both to Cu(I) complexes with carbon monoxide and with chloride, whereas for higher chloride concentrations (greater than [$Cu^{2+}$], about 2 mM), only the $Cu^{2+}/CuCl_n^{(n-1)}$ process was seen; this is consistent, under these experimental conditions, with simple competition between chloride and carbon monoxide for the available Cu(I). Such a result is surprising in view of the many past studies on Cu(I) chloride based carbon monoxide absorbing solutions, in which excess chloride was added.

Furthermore, there was no significant effect in the cyclic voltammetry of Cu(II) reduction to Cu(I) carbonyl on varying the ionic strength (0.01-1.0M $NaClO_4$).

The sensitivity of a detector to substances other than the desired analyte is of considerable importance; the extent of the detrimental effects of an interfering species will depend upon the application. With amperometric carbon monoxide sensors, there is often a cross sensitivity to other oxidizable gases, for example, methane, hydrogen, ethanol vapour, etc., as a consequence of the very positive potential required for the oxidation of carbon monoxide.

As a consequence of the relatively negative potential required for reducing cupric ion in the presence of carbon monoxide, no difference was observed in the cyclic voltammograms of aqueous Cu(II) sulfate after saturating the solution with either hydrogen or methane (natural gas supply) compared to nitrogen. Furthermore, the presence of acetone or ethanol had little effect. Indeed, solutions composed of up to 10% acetone or ethanol behaved similarly to those which were free of organic solvent.

Figure 4:
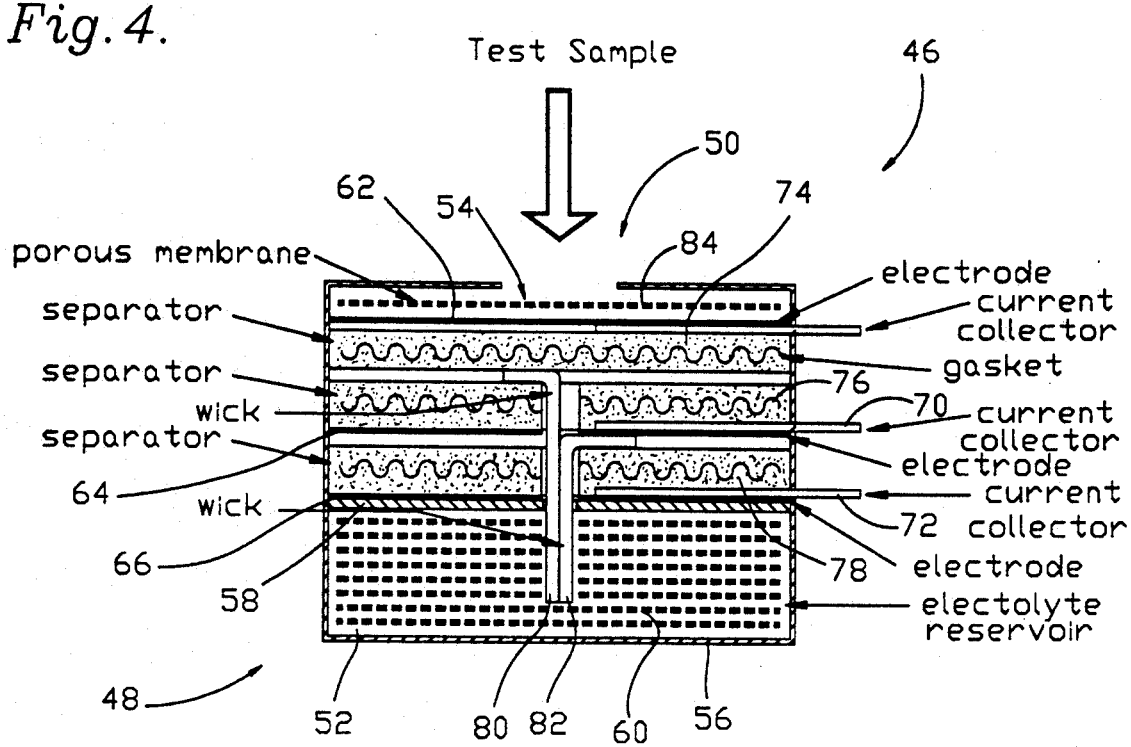
FIG. 4 is a schematic illustration of carbon monoxide detecting apparatus in accordance with the invention useful for field testing of samples.

FIG. 4 is a schematic representation of a detection apparatus 46 adapted for field use. The depicted apparatus is very similar to that disclosed in U.K. published application No. 2,094,055, which is incorporated by reference herein. Broadly speaking, the apparatus 46 includes a casing 48 presenting a test sample inlet opening 50, an electrolyte reservoir 52, and a stacked, sandwich-type cell assembly 54.

In more detail, the casing 48 is simply an appropriately shaped synthetic resin or metallic body 56 of convenient size to house the necessary components of the apparatus 46. A schematically illustrated inlet opening 50 permits introduction of a test sample into the confines of the casing.

The internal construction of the casing 48 includes a lower, apertured wall 58 which defines, with the lower portions of the casing, the reservoir 52; the latter holds a supply of liquid electrolyte 60 of the type previously described.

The cell assembly 54 includes a total of three vertically separated electrodes, namely an uppermost working electrode 62, a central, centrally apertured reference electrode 64 and a lowermost, centrally apertured secondary electrode 66. The working electrode is advantageously formed of carbon cloth or carbon deposited onto a porous membrane. The reference electrode may be formed of any suitable material, so long as it is stable in aqueous solution and will not introduce contaminating ions. The secondary electrode again can be formed of many materials, for example, platinum. It will further be perceived that each electrode has a conductive current collector lead 68, 70, or 72 in operative, electrical contact therewith and extending outwardly through the sidewall of casing 48. These leads may be formed of platinum for example and are adapted for operative connection to a potentiostat during field use.

The cell assembly 54 also includes a total of three vertically spaced, porous separators 74, 76 and 78, which may be formed of an appropriate material such as borosilicate glass fiber filter mat or polyester fiber mat. As illustrated, the uppermost separator 74 underlies and supports the electrode 62 and lead 68; the apertured central separator 76 is positioned atop electrode 64 and lead 70; and the apertured lower separator 78 is positioned atop electrode 66 and lead 72. The respective separators are as noted formed of porous material for permitting absorption and transfer of electrolyte therein.

Operative connection between the electrolyte 60 and the respective electrodes is afforded by means of wicks 80 and 82. As will be seen, the wick 80 extends upwardly from reservoir 52 through the apertures provided in wall 58, electrode 66, separator 78, electrode 64 and separator 76, so as to engage the opposed surfaces of the uppermost separator 74 and central separator 76. Similarly, wick 82 extends upwardly from reservoir 52 through the apertures provided in wall 58, electrode 66 and separator 64, in order to engage the opposed surfaces presented by electrode 64 and lowermost separator 78. The wicks 80, 82 are also absorbent and may be formed of the same material as the respective separators 74-78. Those skilled in the art will perceive that the wicks 80, 82 serve to transfer electrolyte throughout the cell assembly 54 via the absorbent separators.

A porous membrane 84 is provided between sample inlet 50 and the cell assembly 54. This membrane is typically formed of porous teflon and serves to create appropriate gas flow introduction into the cell assembly.

In the use of apparatus 46, the leads 68-72 are connected to a potentiostat such as potentiostat 28 described previously. The latter is then coupled with an appropriate output device, such as a chart recorder or digital readout giving direct carbon monoxide concentrations. A gas sample may then be introduced through opening 50 into the confines of cell 54, whereupon the gas diffuses through membrane 84 and passes into the cell proper. Inasmuch as the respective electrodes are in operative contact with the electrolyte 60 through the described wick/separator system, the detection proceeds in a manner identical to that described in reference to the laboratory-type apparatus 10.

We claim:

1. An apparatus for determining the presence of carbon monoxide in a test sample, said apparatus comprising:
   an electrical cell assembly including a quantity of electrolyte having hydrated Cu(II) ions therein, and a pair of electrodes in operative contact with said electrolyte;
   means for introducing said test sample inot said apparatus in the region of said operative contact between said electrolyte and said electrodes;
   means including said electrodes and electrolyte for creating an electrical potential difference between the electrodes of a magnitude of +0.03 to +0.15 volts which favors the reduction of said Cu(II) ions to Cu(I) ions and the formation of Cu(I)-carbonyl complexes by reaction between the Cu(I) ions and carbon monoxide present in said test sample; and
   detecting means including structure for detecting an electrical parameter indicative of said reduction of Cu(II) ions to Cu(I) ions.

2. The apparatus of claim 1, said electrolyte comprising an aqueous mixture including therein respective quantities of copper sulfate and a member selected from the group consisting of sodium perchlorate, sodium trifluoroacetate, sodium tetrafluoroborate, sodium trifluoromethylsulfate, potassium hexafluorophosphate, sodium sulfate, sodium acetate, potassium hydrogen phosphate, potassium phthalate, methylsulfonate, phenylsulfonate, nitrate salts, and mixtures thereof.

3. The apparatus of claim 2, said copper sulfate being present at a level of from about 0.5 mM to 10 mM in said electrolyte.

4. The apparatus of claim 2, said member being present in said mixture at an excess of from about 10 to 100 times the concentration of said copper sulfate.

5. The apparatus of claim 2, said electrolyte including a quantity of sodium perchlorate.

6. The apparatus of claim 4, said sodium perchlorate being present at a level of from about 0.01M to 1M.

7. The apparatus of claim 1, said electrolyte comprising an aqueous mixture and having a pH of up to about 6.5.

8. The apparatus of claim 7, said pH being from about 1 to 6.

9. The apparatus of claim 1, said electrolyte being essentially free of interfering amounts of species which will coordinate with Cu(I) ions.

10. The apparatus of claim 1, the concentration of Cu(II) ions in said electrolyte being sufficiently in excess of the concentration of carbon monoxide in said test sample to assure that the mass transfer of carbon monoxide in the apparatus determines the rate of formation of said Cu(I)-carbonyl complexes.

11. The apparatus of claim 1, including a secondary electrode in operative contact with said electrolyte and operatively coupled with said detecting means.

12. The apparatus of claim 1, said detecting means including a potentiostat operatively coupled with said electrodes for establishing and maintaining an essentially constant potential difference between the electrodes, said detecting structure including means for detecting the response current generated between the electrodes.

13. A method of determining the presence of carbon monoxide in a test sample, said method comprising the steps of:
   providing a cell assembly including a quantity of an electrolyte having hydrated Cu(II) ions therein, with a pair of electrodes in operative contact with said electrolyte;
   introducing said test sample into the region of operative contact between said electrodes and said electrolyte;
   creating an electrical potential difference between said electrodes of a magnitude preferentially favoring the reduction of said Cu(II) ions to Cu(I) ions and the formation of Cu(I)-carbonyl complexes by the reaction of said Cu(I) ions and carbon monoxide from said test sample; and
   detecting an electrical parameter indicative of said reduction of Cu(II) ions to Cu(I) ions.

14. The method of claim 13, said electrolyte comprising an aqueous mixture including therein respective quantities of copper sulfate and a member selected from the group consisting of sodium perchlorate, sodium trifluoroacetate, sodium tetrafluoroborate, sodium trifluoromethylsulfate, potassium hexafluorophosphate, sodium sulfate, sodium acetate, potassium hydrogen phosphate, potassium phthalate, methylsulfonate, phenylsulfonate, nitrate salts, and mixtures thereof.

15. The method of claim 14, said copper sulfate being present at a level of from about 0.5 mM to 10 mM in said electrolyte.

16. The method of claim 14, said member being present in said mixture at an excess of from about 10 to 100 times the concentration of said copper sulfate.

17. The method of claim 14, said electrolyte including a quantity of sodium perchlorate.

18. The method of claim 16, said sodium perchlorate being present at a level of from about 0.01M to 1M.

19. The method of claim 13, said electrolyte comprising an aqueous mixture and having a pH of up to about 6.5.

20. The method of claim 19, said pH being from about 1 to 6.

21. The method of claim 13, said electrolyte being essentially free of interfering amounts of species which will coordinate with Cu(I) ions.

22. The method of claim 13, the concentration of Cu(II) ions in said electrolyte being sufficiently in excess of the concentration of carbon monoxide in said test sample to assure that the mass transfer of carbon monoxide in the apparatus determines the rate of formation of said Cu(I)-carbonyl complexes.

23. The method of claim 13, said detecting step comprising the steps of creating and maintaining a substantially constant potential difference between said electrodes, and detecting the response current generated between said electrodes.

24. The method of claim 13, said electrical potential difference between said electrodes having a magnitude of from about +0.03 to +0.15 volts.

* * * * *